United States Patent [19]
Boutos

[11] Patent Number: 6,151,527
[45] Date of Patent: Nov. 21, 2000

[54] ELECTRODE APPARATUS FOR STIMULATING LIVING TISSUE

[76] Inventor: David Boutos, 4420 Dunlap Crossing St., Las Vegas, Nev. 89129

[21] Appl. No.: 09/212,655

[22] Filed: Dec. 16, 1998

[51] Int. Cl.[7] ............................... A61N 1/05; A61N 1/00
[52] U.S. Cl. ............................ 607/138; 607/143; 607/39
[58] Field of Search ................................... 607/119, 122, 607/138, 143, 39

[56] References Cited

U.S. PATENT DOCUMENTS

| | | |
|---|---|---|
| 5,456,709 | 10/1995 | Hamedi . |
| 5,571,118 | 11/1996 | Boutos . |
| 5,697,966 | 12/1997 | Boutos . |
| 5,782,902 | 7/1998 | Boutos . |
| 5,875,778 | 3/1999 | Vroegop . |

*Primary Examiner*—Carl H. Layno
*Attorney, Agent, or Firm*—Meschkow & Gresham P.L.C.; Jordan M. Meschkow; Lowell W. Gresham

[57] ABSTRACT

Electrodes for stimulating living tissue such as vaginal, anal, clitoral, penile, and scrotal tissue are shown. Electrical stimulation to such areas is intended to induce excitation and orgasm in either females or males, particularly where frigidity or impotence is a problem. Four embodiments of the electrode apparatus include a flexible tube shaped base and an electrode either in the form of a loop or a stem coupled to the base. The electrode is formed from one of an electrically-conductive solid cord, an electrically-conductive tube, and an insulated conductor cable. An electrical contact at one end of the electrode allows the electrode to be connected to an electrical source. Auxiliary members such as conductive beads, conductive endpieces, conductive or nonconductive tube shaped coverings, and vibrators are added to any of the electrode apparatuses to impart specific stimuli in specific regions of the user's anatomy.

38 Claims, 11 Drawing Sheets

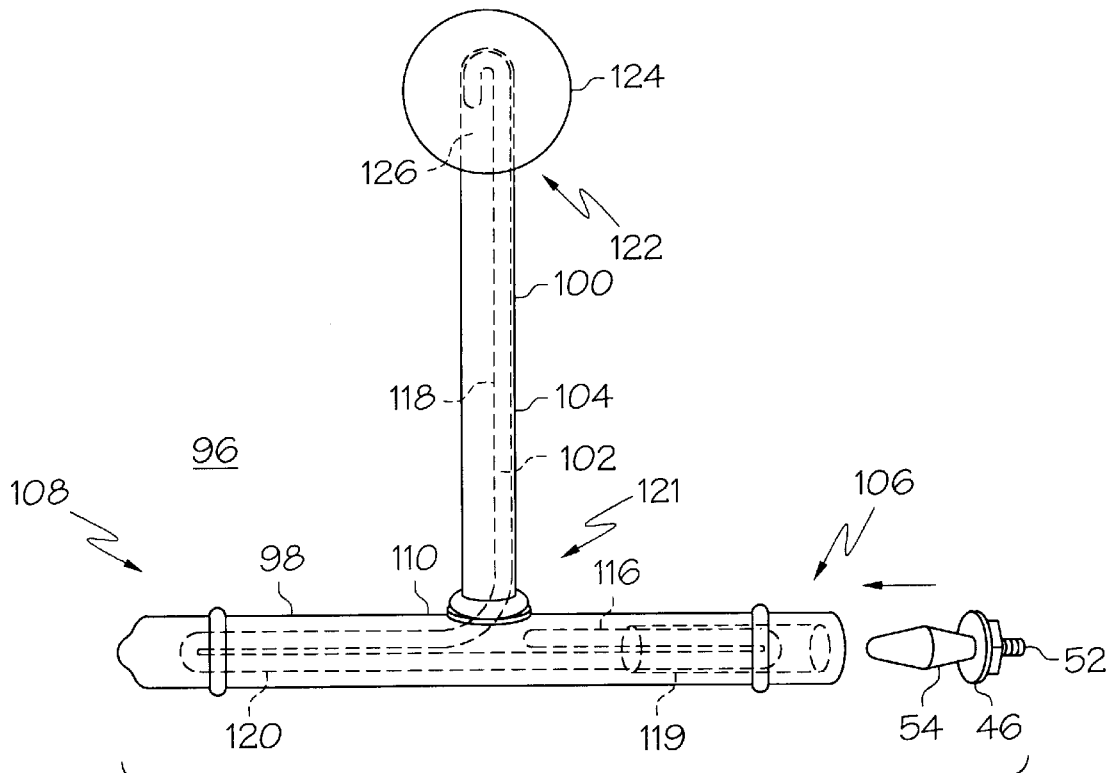
FIG. 8
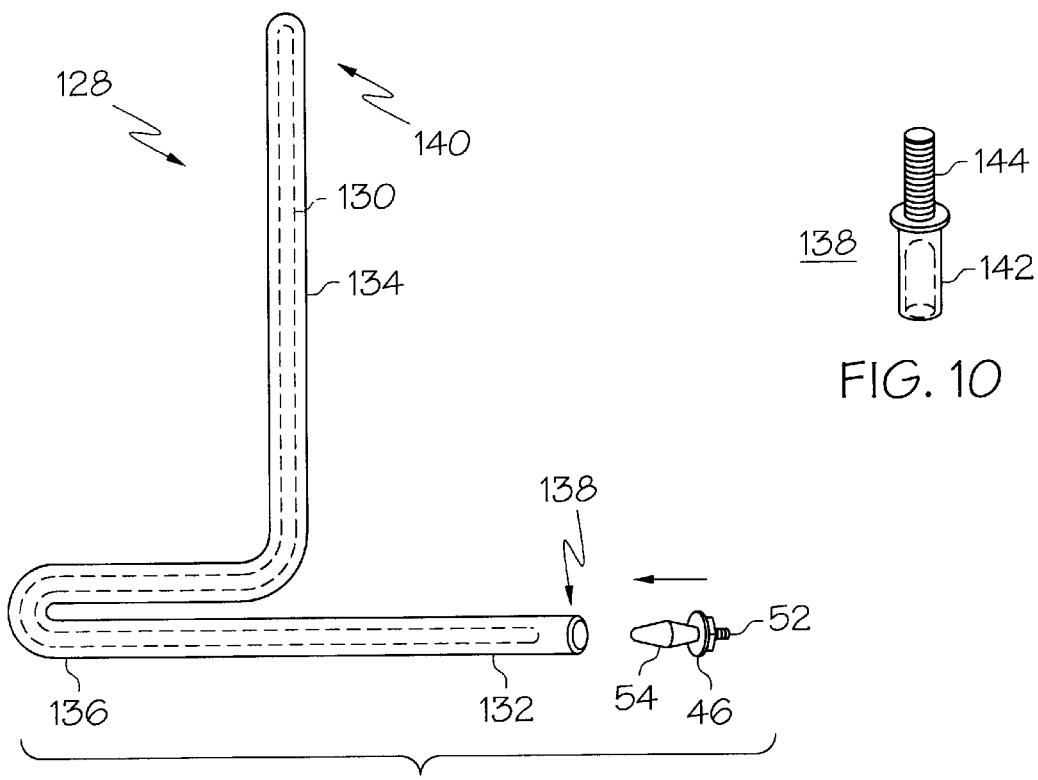
FIG. 10
FIG. 9

---

ELECTRODE APPARATUS FOR STIMULATING LIVING TISSUE

TECHNICAL FIELD OF THE INVENTION

The invention relates to devices for applying electrical energy to living tissue. More particularly, the present invention relates to an apparatus for electrically stimulating penile, scrotal, anal, vaginal, and clitoral tissue.

BACKGROUND OF THE INVENTION

It is known that medical disorders such as diabetes, leukemia, anemia, X-ray exposure, and so forth can cause impotence in males and frigidity in females. Furthermore, it is known that the application of electrical stimulation to penile tissue can cause erection where impotence may exist due to these physiological conditions or due to psychological conditions. Likewise, the application of electrical and vibrational stimulation to female genitalia can cause arousal where frigidity may exist due to these physiological conditions or due to psychological conditions. Indeed, it is known that the application of electrical or vibrational stimulation to penile, vaginal, clitoral, anal, or prostate tissue can induce orgasm, even where the subject has suffered damage to the nerves serving the sex organs.

The art is replete with various devices used to apply electrical stimulation to the subject areas. Rigid rings capable of transmitting low levels of electricity to the skin and muscles are typically applied about the penis and/or the scrotum. Insertable rolled or plug-type electrodes, made to be rolled to size, or sized in a variety of sizes to fit the user's anatomy, are known for the purpose of applying low levels of electricity to the skin and muscles inside and surrounding the penis, the vagina, and the anus.

Rigid rings are useable for males where the application of electrical current to only a portion of penile tissue is sufficient to induce erection. However, the rigid ring is not useable for internal application, such as in the vagina or in the anus, due to its rigidity and relatively large size. This is especially problematic for females since the female genitalia are largely internal organs.

For both males and females, internally worn insertable electrodes are desirable to stimulate and to induce orgasm. However, many of these prior art insertable electrodes are difficult to retain in the appropriate position, uncomfortable for prolonged wear due to rigid components, and hard to effectively clean.

In addition to devices used to apply electrical stimulation, the art is replete with various devices used to apply vibrational stimulation. Vibrational stimulation is particularly effective for the stimulation of clitoral tissue. However, no known prior art devices safely and conveniently provide both vibrational and electrical stimulation to a subject area or areas.

It would be highly advantageous, therefore, to remedy the foregoing and other deficiencies inherent in the prior art.

SUMMARY OF THE INVENTION

Accordingly, it is an object of the present invention to provide improvements in electrical stimulation apparatus for both men and women.

Another object of the invention is to provide improved means for the application of electrical stimulation to the anal, vaginal, clitoral, penile, and scrotal tissue.

Yet another object of the invention is to provide male stimulation apparatus that can induce erection and orgasm, and female electrical stimulation apparatus that can induce orgasm.

A further object of the invention is to provide means for the application of both electrical and vibrational stimulation to the anal, vaginal, and clitoral tissue.

The above and other advantages of the present invention are carried out in one form by an electrode apparatus which includes a base having a length, and first and second ends located at opposite ends of said length, an exterior surface, an interior passage, and a hole running from the exterior surface to the interior passage. An electrode has a first section residing in the interior passage of the base, and a second section extending from the exterior surface of the base from the hole. An electrical contact is in electrical communication with the electrode. A first plug is connected to the first end and a second plug is connected to the second end. The first plug has an opening through which a portion of the electrical contact extends.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

FIG. 8 shows the perspective view of the electrode apparatus of FIG. 7 illustrating its internal wiring in hidden lines;

FIG. 9 shows an alternative electrode which may be used in place of the electrode in the electrode apparatus of FIG. 8;

FIG. 10 shows a perspective view of an electrically-conductive connector for attaching an auxiliary member in the form of a spherical endpiece to the electrode of FIG. 9;

DETAILED DESCRIPTION OF THE PREFERRED EMBODIMENTS

Figure 1:
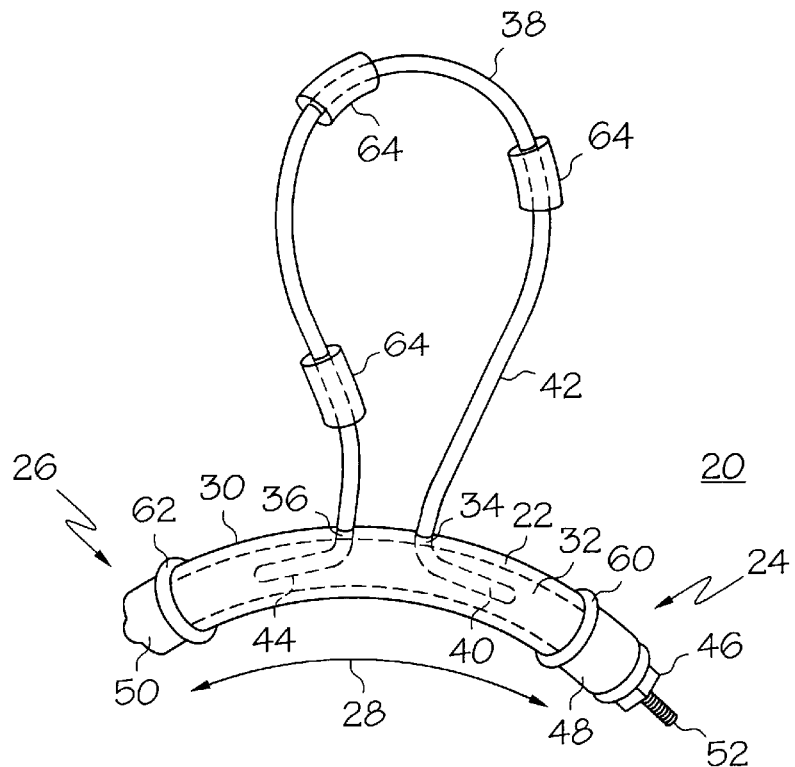
FIG. 1 shows a perspective view of an electrode apparatus in accordance with the present invention.
Figure 2:
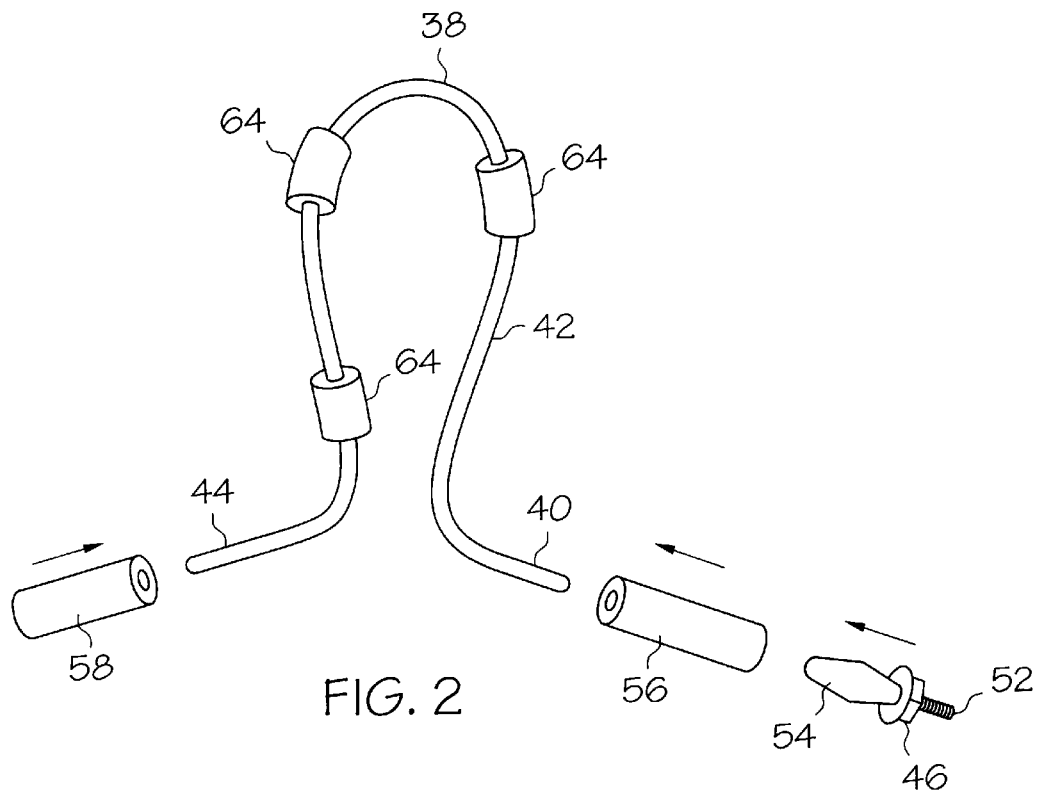
FIG. 2 shows an exploded perspective view of the electrical communication path of the electrode apparatus.

Turning now to the drawings in which like reference characters indicate corresponding elements throughout the several views, attention is first directed to FIGS. 1–2 where an electrode apparatus 20 is shown. FIG. 1 shows a perspective view of electrode apparatus 20 in accordance with the present invention. FIG. 2 shows an exploded perspective view of the electrical communication path of electrode apparatus 20.

Electrode apparatus 20 includes a tube-shaped base 22 which has a first end 24 and a second end 26 located at opposite ends of a length 28 of base 22. Base 22 includes an exterior surface 30 and an interior passage 32. A first hole 34 runs from exterior surface 30 to interior passage 32. Likewise, a second hole 36 runs from exterior surface 30 to interior passage 32. In the preferred embodiment, base 22 is fabricated from an elastomeric material such as silicon, viton, or neoprene, such material being nonconductive, flexible, and readily cleanable.

An electrode 38 includes a first section 40, a second section 42, and a third section 44. Electrode 38 is disposed in base 22 by inserting electrode 38 through first hole 34 such that first section 40 resides in interior passage 32 proximate first end 24. Second section 42 extends from exterior surface 30 of base 22 from first hole 34 to second hole 36 to form a loop. Third section 44 of electrode 38 is disposed in base 22 by inserting third section 44 through second hole 36 such that third section 44 resides in interior passage 32 proximate second end 26.

Electrode 38 is a solid conductive cord desirably fabricated from an elastomeric material such as silicon, viton, or neoprene for comfort and cleanability. Electrode 38 is flexible so that electrode 38 can adapt to the particular anatomy in which it will be inserted. Electrode 38 is made conductive along the length of electrode 38 by embedding carbon particles in the elastomeric material during fabrication.

Electrode apparatus 20 further includes an electrical contact 46, a first plug 48 connected to first end 24, and a second plug 50 connected to second end 26. First plug 48 includes an opening (not shown) through which a first portion 52 of electrical contact 46 extends.

With particular reference to FIG. 2, a second portion 54 of electrical contact 46 plugs directly into one end of a first tubular sheath 56. Likewise, first section 40 of electrode 38 plugs directly into the other end of first tubular sheath 56. First tubular sheath 56 is fabricated from an elastomeric material and made conductive by embedded carbon particles so that first tubular sheath 56 forms a path for electrical communication between electrical contact 46 and electrode 38. Third section 44 of electrode 38 plugs directly into a second tubular sheath 58. Second tubular sheath 58 is also fabricated from an elastomeric material. However, second tubular sheath 58 need not be made conductive.

First and second tubular sheaths 56 and 58, respectively, are configured to retain first and second sections 40 and 44, respectively, of electrode 38 through a friction fit. In addition, first tubular sheath 56 is configured for press-fit into interior passage 32 of base 22 proximate first end 24 while second tubular sheath 58 is configured for press-fit into interior passage 32 of base 22 proximate second end 26.

Following assembly of electrode apparatus 20, a first O-ring 60 is positioned to surround base 22 at first end 24 and a second O-ring 62 is positioned to surround base 22 at second end 26. First O-ring 60 is configured to apply a force sufficient to retain first section 40 and first tubular sheath 56 in base 22. Likewise, second O-ring 62 is configured to apply a force sufficient to retain third section 44 and second tubular sheath 58 in base 22.

Electrode apparatus 20 optionally includes a plurality of auxiliary members in the form of tube-shaped coverings 64. Tube-shaped coverings 64 are slidably adjustable to a plurality of positions along the length of second section 42 of electrode 38. Tube-shaped coverings 64 may be conductive of electrical current for providing a concentrated electrical stimulus on the body tissue contacting tube-shaped coverings 64. Alternatively, tube-shaped coverings 64 may be nonconductive of electrical current, so that no electrical stimulus is imparted on the body tissue in contact with tube-shaped coverings 64. Accordingly, tube-shaped coverings 64 allow electrode apparatus 20 to be configurable according to the user's preferences for degree and location of electrical stimulus.

Figure 14:
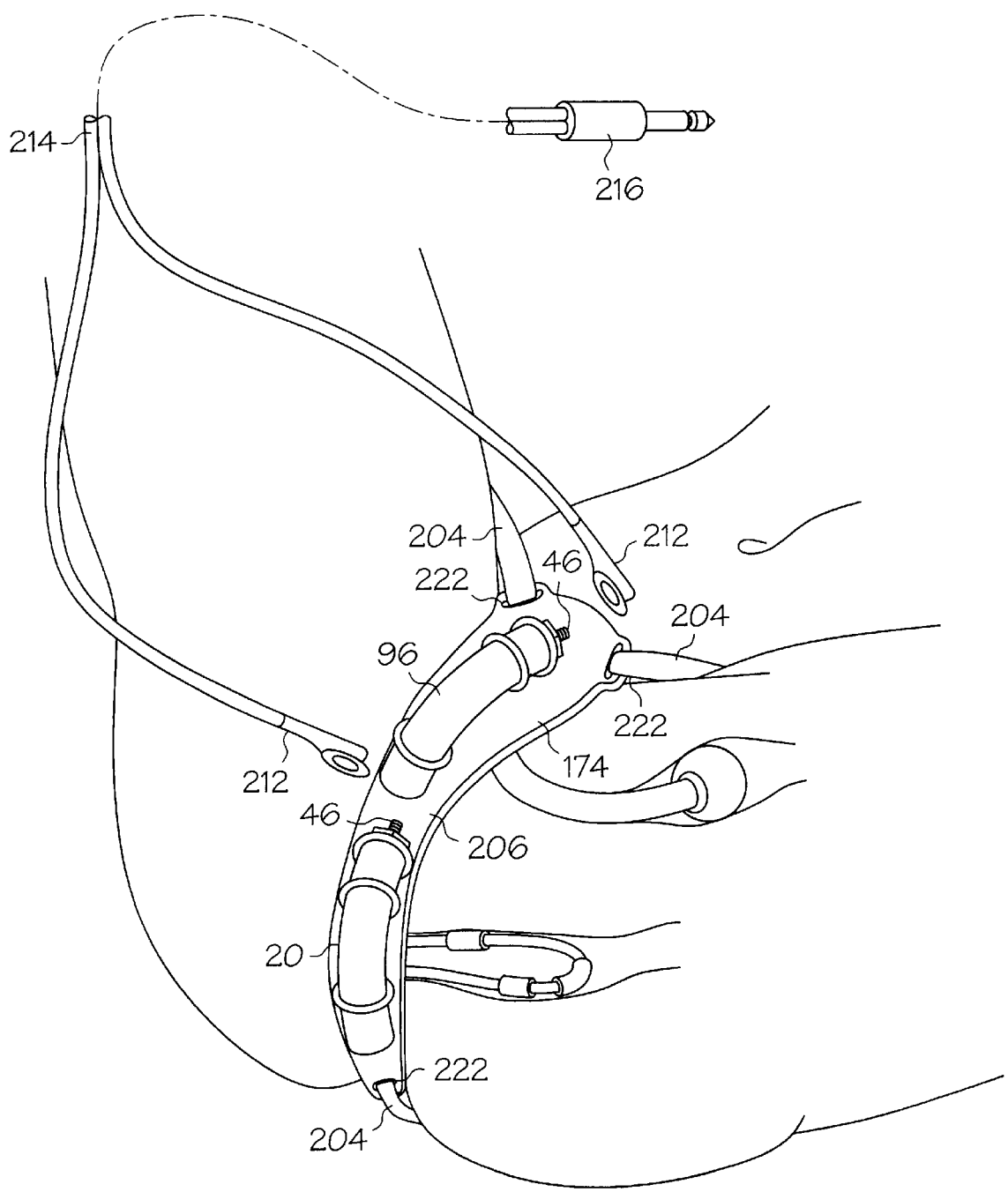
FIG. 14 shows the electrode apparatus in the configuration shown in FIG. 1 used in combination with the electrode apparatus in the configuration shown in FIG. 7.

Once electrode apparatus 20 is assembled, first portion 52 of electrical contact 46 extends from first end 24 of base 22. First portion 52 conducts electricity to electrode 38 through second portion 54 of electrical contact 46 and first tubular sheath 56 when first portion 52 is connected to a source of electricity, typically a controller allowing for adjustment of current (not shown). The controller will typically include a jack, and a wire connected to the jack. The wire will typically terminate with a connector which is configured for attachment to first portion 52. Such a connector is shown in FIG. 14.

Figure 3:
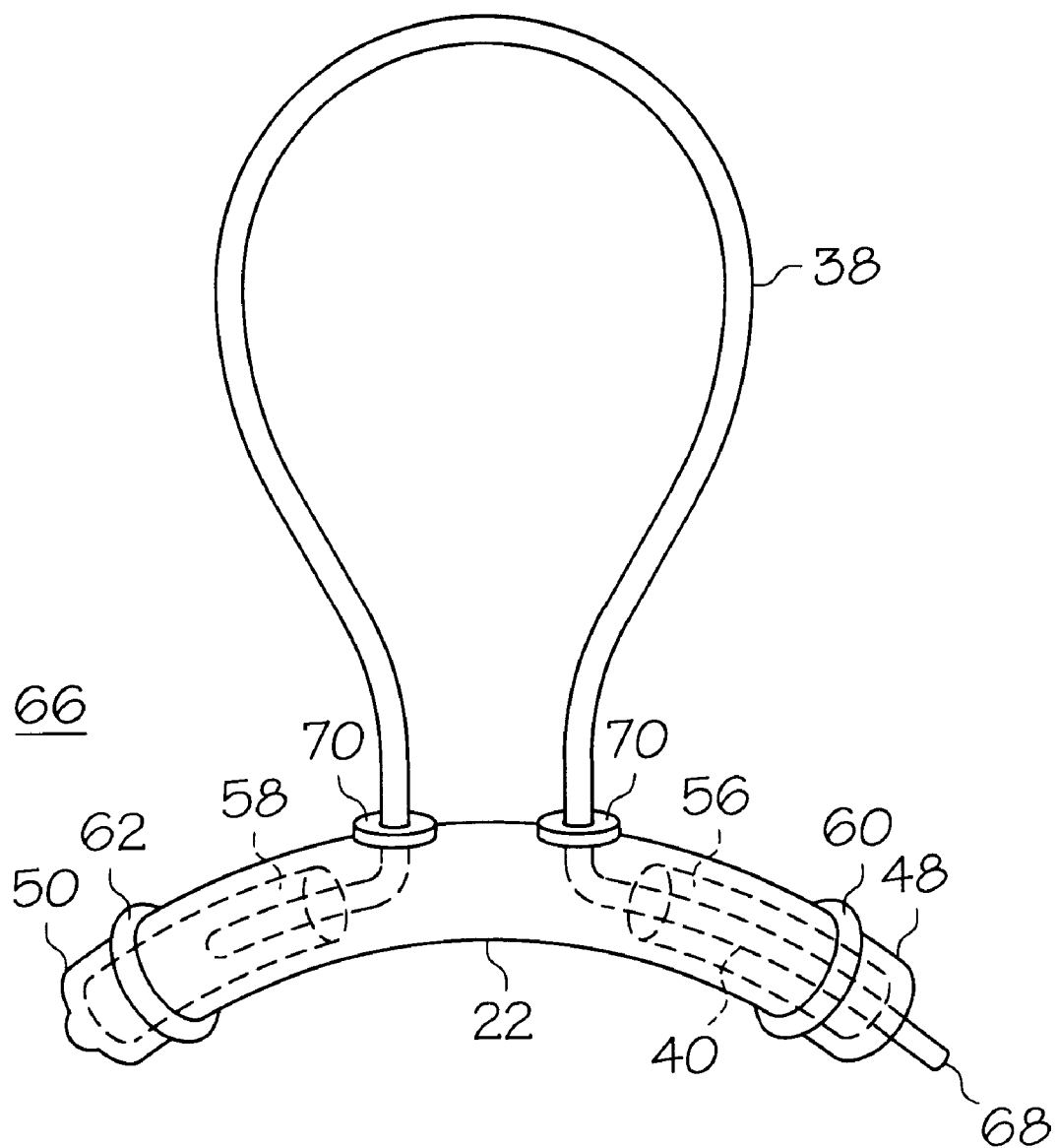
FIG. 3 shows a perspective view of an alternative embodiment of the electrode apparatus in accordance with the present invention.

FIG. 3 shows a perspective view of an alternative electrode apparatus 66 in accordance with the present invention. Electrode apparatus 66 includes base 22, electrode 38, first plug 48, and second plug 50, first tubular sheath 56, and second tubular sheath 58, first O-ring 60, and second O-ring 62 all of which have been described above. Electrode apparatus 66 further includes an extended segment 68 of first section 40 which extends through the opening (not shown) of first plug 48. Since, electrode 38 is conductive along its length, extended segment 68 may be connected directly to a connector for receiving electrical current from a source of electricity (not shown). Thus, electrode apparatus 66 is simple and cost effective to assemble.

Electrode apparatus 66 includes O-rings 70 surrounding electrode 38 and abutting base 22 at each of first and second holes 34 and 36, respectively. O-rings 70 serve to provide stable fixation points for the coupling of electrode 38 with base 22. It should be readily apparent that O-rings 70 may also be included on electrode apparatus 20 (FIG. 1).

Figure 4:
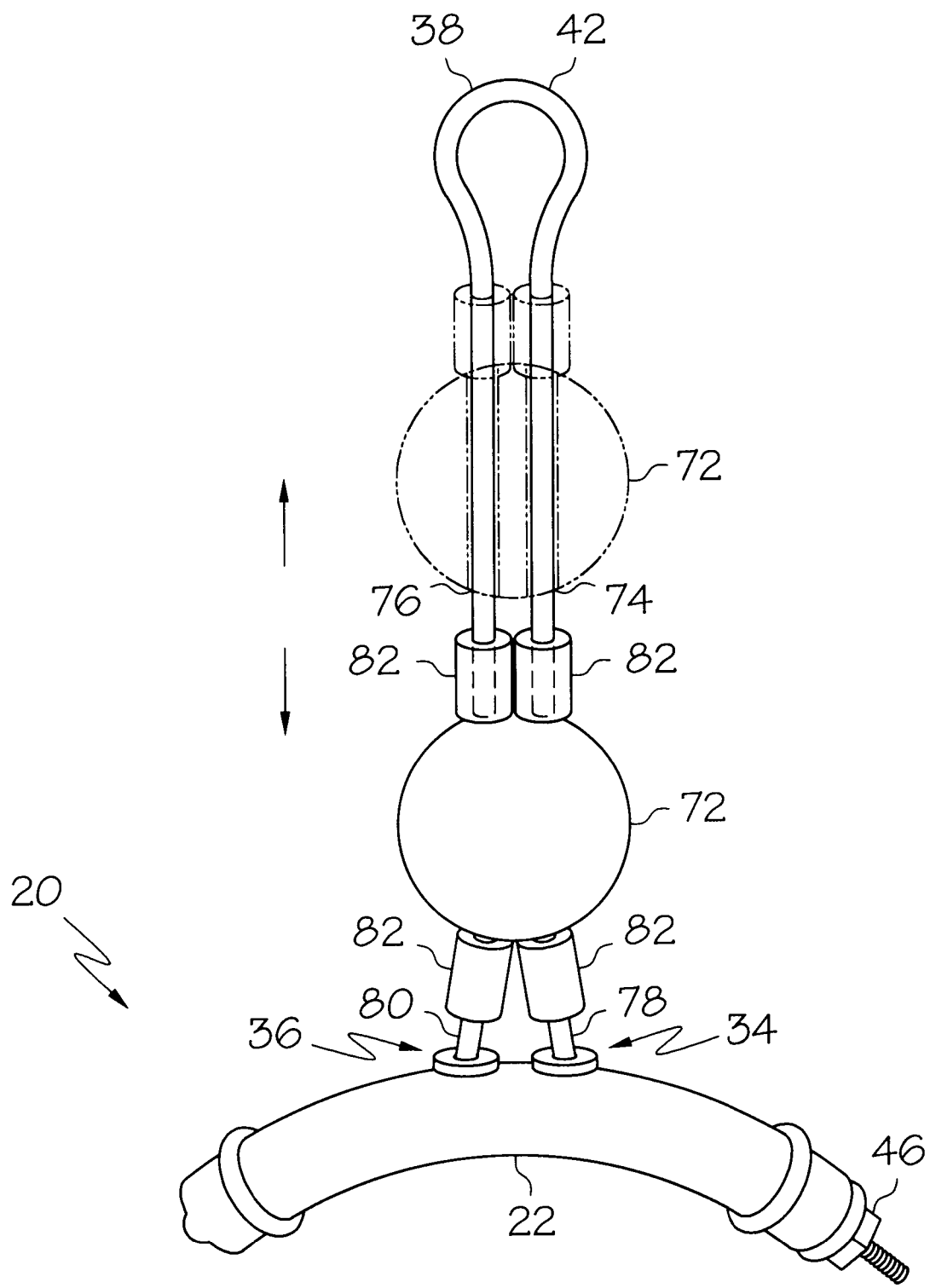
FIG. 4 shows a perspective view of an auxiliary member slidably coupled to the electrode apparatus.

FIG. 4 shows a perspective view of an auxiliary member 72 slidably coupled to electrode apparatus 20. Auxiliary member 72 is in the form of a conductive, spherical bead having a first aperture 74 and a second aperture 76, shown in hidden lines, extending through spherical bead 72. First and second apertures 74 and 76, respectively, are substantially parallel, and are arranged so that a first end 78 of second section 42 is directed through first aperture 74 to first hole 34 and a second end 80 of second section 42 is directed through second aperture 76 to second hole 36.

Electrode apparatus 20 also includes adjustable stops 82. Adjustable stops 82 are tube shaped nonconductive auxiliary members that are arranged to prevent movement of spherical bead 72 when spherical bead 72 is in a desired position on second section 42. Adjustable stops 82 and spherical bead 72 may be slid along second section 42 to any of a number of positions, one of which is shown in phantom. Since spherical bead 72 and electrode 38 are electrically conductive, spherical bead 72 may be arranged to deliver a concentrated electrical stimulus to a desired position according to a user's preferences.

Figure 5:
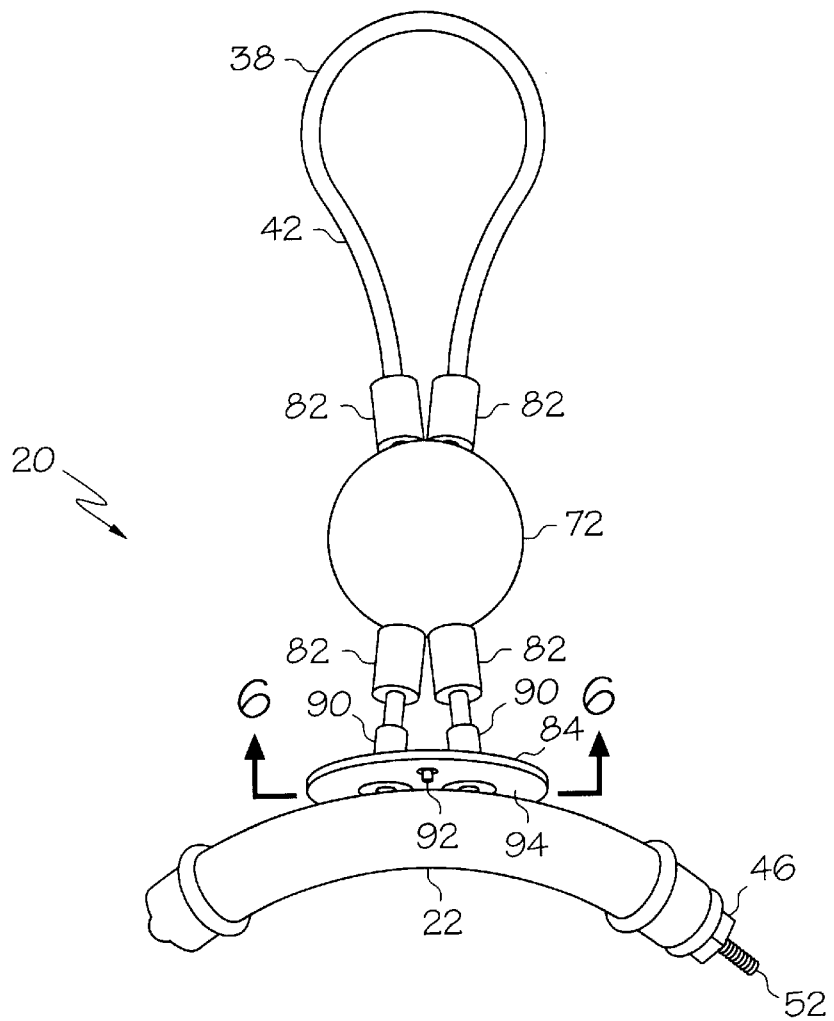
FIG. 5 shows a perspective view of the electrode apparatus with a spherical auxiliary member and a plate shaped auxiliary member.
Figure 6:
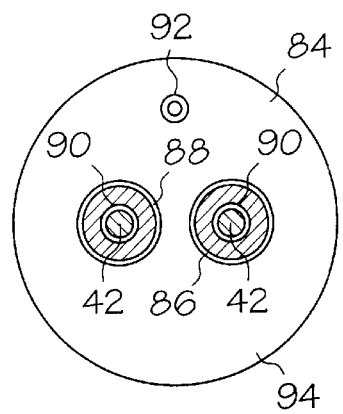
FIG. 6 shows a sectional view 6—6 of the electrode apparatus of FIG. 5.

Referring to FIGS. 5–6, FIG. 5 shows a perspective view of electrode apparatus 20 with spherical bead 72 and a second auxiliary member in the form of a conductive, flexible plate 84. FIG. 6 shows a sectional view 6—6 of electrode apparatus 20 of FIG. 5. Extending therethrough conductive plate 84 is a first hole 86 and a second hole 88. Electrically-nonconductive grommets 90 are positioned in each of first and second holes 86 and 88, respectively, and second section 42 of electrode 38 is directed through grommets 90.

An electrically-conductive snap attachment 92 is located on an outside surface 94 of conductive plate 84. Conductive plate 84 is fabricated from an elastomeric material such as silicon, viton, or neoprene, made conductive by embedding carbon particles in the elastomeric material during fabrication. The location of grommets 90 cause electrode 38 and conductive plate 84 to be electrically insulated from one another. Accordingly, one of the contacts of an electrical source, shown in FIG. 14, may be attached to first portion 52 of electrical contact 46 and the other contact of the electrical source may be attached to snap attachment 92 of conductive plate 84.

When in use, electrode apparatus 20, shown in FIG. 5, is positioned so that spherical bead 72 is located in the vagina and conductive plate 84 rests against the external female genitalia. In this position, spherical bead 72 and electrode 38 provide electrical stimulation to vaginal tissue while conductive plate 84 provides electrical stimulation to clitoral tissue.

Figure 7:
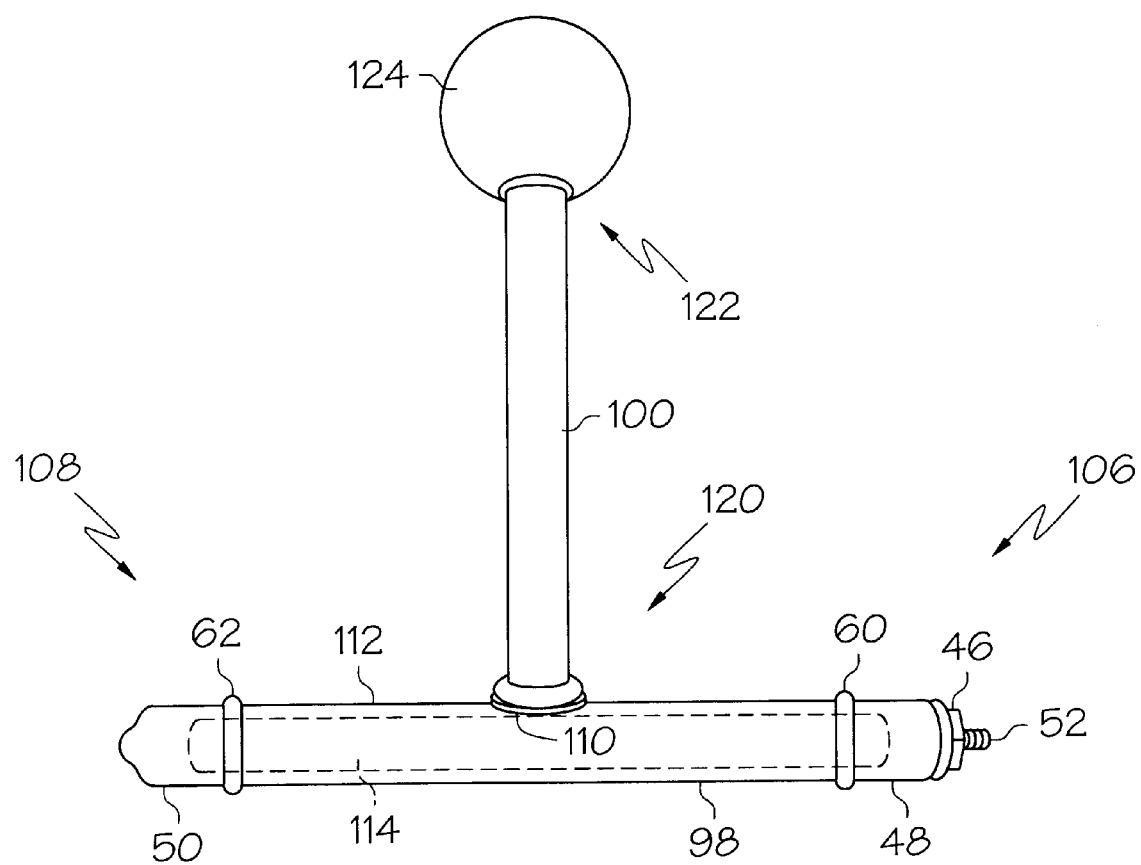
FIG. 7 shows a perspective view of a third embodiment of the electrode apparatus in accordance with the present invention.

With reference to FIGS. 7–8, FIG. 7 shows a perspective view of an alternative electrode apparatus 96 in accordance with the present invention. FIG. 8 shows the perspective view of the electrode apparatus of FIG. 7 illustrating its internal wiring in hidden lines. Electrode apparatus 96 is particularly effective for vaginal placement and electrical stimulation of vaginal tissue.

Electrode apparatus 96 includes a flexible, tube-shaped base 98 and an electrode in the form of a stem electrode 100. Stem electrode 100 includes a deformable wire 102 surrounded by an electrically insulative material 104. Base 98 includes first and second ends 106 and 108, respectively, located at opposite ends of the length of base 98. Like electrode apparatus 20 (FIG. 1), electrode apparatus 96 further includes electrical contact 46, first plug 48 connected to first end 106, and second plug 50 connected to second end 108. First plug 48 includes an opening (not shown) through which first portion 52 of electrical contact 46 extends.

A hole 110 runs from an exterior surface 112 of base 98 to an interior passage 114 of base 98. Wire 102 of stem electrode 100 includes a first section 116, a second section 118, and a third section 120. Wire 102 is disposed in base 98 by inserting wire 102 through hole 110 such that first section 116 resides in interior passage 114 proximate first end 106. Second section 118 extends from exterior surface 112 of base 98 from hole 110, and third section 120 of wire 102 is located between and contiguous with first section 116 and second section 118.

Wire 102 has the ability to hold electrode 100 in a formed shape following deformation from an original shape. Thus, during manufacture wire 102 is bent so that first section 116 resides in interior passage 114 proximate first end 106. Wire 102 is then directed along the length of interior passage 114 so that third section 120 resides in interior passage 114 proximate second end 108. Wire 102 is then bent and directed back through interior passage 114 to hole 110 through which second section 118 of wire 102 extends.

Wire 102 of electrode 100 is routed throughout the length of base 98 to allow second end 108 to be bent as desired and to provide second end 108 with structural stability.

Alternatively, third section 120 may be a separate wire (not shown) residing in interior passage 114 proximate second end 108 and wire 102 may include only first and second sections 116 and 118, respectively.

First section 116 resides in a conductive sheath 119 which is press-fit in interior chamber 114 of base 98. During manufacture, second portion 54 of electrical contact 46 is inserted into conductive sheath 119. Thus, conductive sheath 119 forms an electrical communication pathway for the transfer of electrical current from electrical contact 46 to stem electrode 100.

Second section 118 of wire 102 includes a proximal end 121 located proximate hole 110 and a distal end 122 at an opposite ends of the length of second section 118. Second section 118 of wire 102 is encased by insulative material 104 along the length of second section 118 except for distal end 122.

An auxiliary member in the form of a conductive, spherical endpiece 124 is positioned at distal end 122. Endpiece 124 may be formed from a conductive ceramic, a conductive plastic or rubber, or a metal such as brass. Those skilled in the art will recognize that endpiece 124 need not be spherical in shape. Rather, endpiece 124 may be oblong, ellipsoid, hemispherical, or any other shape that may be comfortably inserted into the vagina.

Spherical endpiece 124 includes an aperture 126 having a depth which is less than a thickness of endpiece 124. In other words, aperture 126 extends into, but not completely through, endpiece 124. During manufacture, distal end 122 of wire 102 is inserted and retained by press-fitting distal end 122 in aperture 126. Distal end 122 may be bent to increase the size wire 102 for a more secure fit in aperture 126.

FIG. 9 shows an alternative electrode 128 which may be used in place of electrode 100 (FIG. 8) in electrode apparatus 96 (FIG. 8). Electrode 128 is a tubular electrode fabricated from carbon-embedded elastomeric material such as low modulus silicon, viton, and neoprene, thereby rendering all of tube electrode 128 conductive.

Embedded within tube electrode 128 is a wire 130. Wire 130 is not necessarily intended to carry electricity, but when within electrode 128, allows the bending of electrode 128 and retains the bent angle of electrode 128. Such bending and "memory" posturing allows tube electrode 128 to be effectively positioned within the cavity inserted.

Tube electrode 128 includes a first section 132, a second section 134, and a third section 136. Since, wire 130 has the ability to hold electrode 128 in a formed shape, during manufacture tube electrode 128 is bent so that first section 132 resides in interior passage 114 (FIG. 7) proximate first end 106 (FIG. 7). Tube electrode 128 is then directed along the length of interior passage 114 so that third section 136 resides in interior passage 114 proximate second end 108 (FIG. 7). Tube electrode 128 is then bent and directed back through interior passage 114 to hole 110 (FIG. 7) through which second section 134 of tube electrode 128 extends.

Second portion 54 of electrical contact 46 is then plugged directly into tube electrode 128 at an end 138 of first section 132 so that second portion 54 extends into tube electrode 128 and first portion 52 extends from end 138 of first section 132 of tube electrode 128. Second portion 54 is retained in tube electrode 128 through friction fit. Accordingly, when first portion 52 is connected to a power source (not shown) electrical current is conveyed from electrical contact 46 directly to tube electrode 128. Thus, electrode apparatus 96 (FIG. 7) with tube electrode 128 is inexpensive and simple to manufacture.

Second section 134 of tube electrode 128 is configured to accommodate an alternative means for coupling spherical endpiece 124 (FIG. 8) to electrode 128. FIG. 10 shows a perspective view of an electrically-conductive connector 138 for attaching spherical endpiece 124 to a distal end 140 (FIG. 9) of second section 134. Connector 138 has a tubular end 142 and a threaded end 144. Tubular end 142 is sized for press-fit with distal end 140 of second section 134.

When used with connector 138, aperture 126 (FIG. 8) of spherical endpiece 124 includes threads (not shown) which may be removably mated with threaded end 144 of connector 138. Thus, endpiece 124 is securely retained on tube electrode 128 when in use, but may be readily removed for cleaning or replacement. Connector 138 is described in connection with tube electrode 128 for clarity of illustration. However, it should be apparent to those skilled in the art that connector 138 may also be used with stem electrode 100 (FIG. 8).

Figure 11:
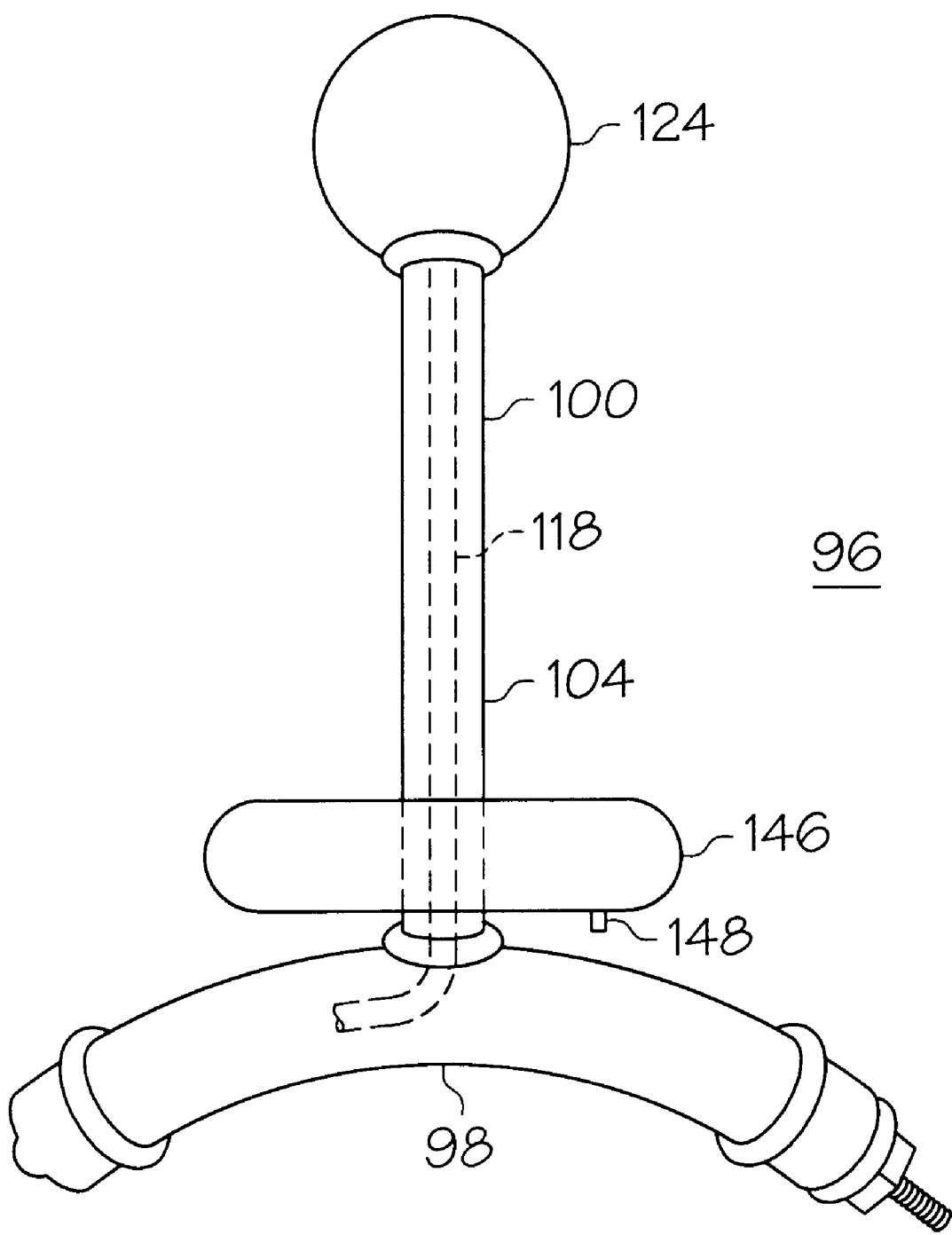
FIG. 11 shows an additional feature that may be incorporated into the electrode apparatus of FIG. 7.

FIG. 11 shows an additional feature that may be incorporated into electrode apparatus 96 (FIG. 7). An oblong auxiliary member in the form of a vibrator 146 is positioned on electrode 100. Vibrator 146 includes a connector 148 which may be connected to a power source (not shown) in order to energize vibrator 146. When in use, electrode apparatus 96, shown in FIG. 11, is positioned so that spherical endpiece 124 is located in the vagina and vibrator 146 rests against the external female genitalia. In this position, spherical endpiece 124 provides electrical stimulation to vaginal tissue while vibrator 146 provides vibrational stimulation to clitoral tissue.

Figure 12:
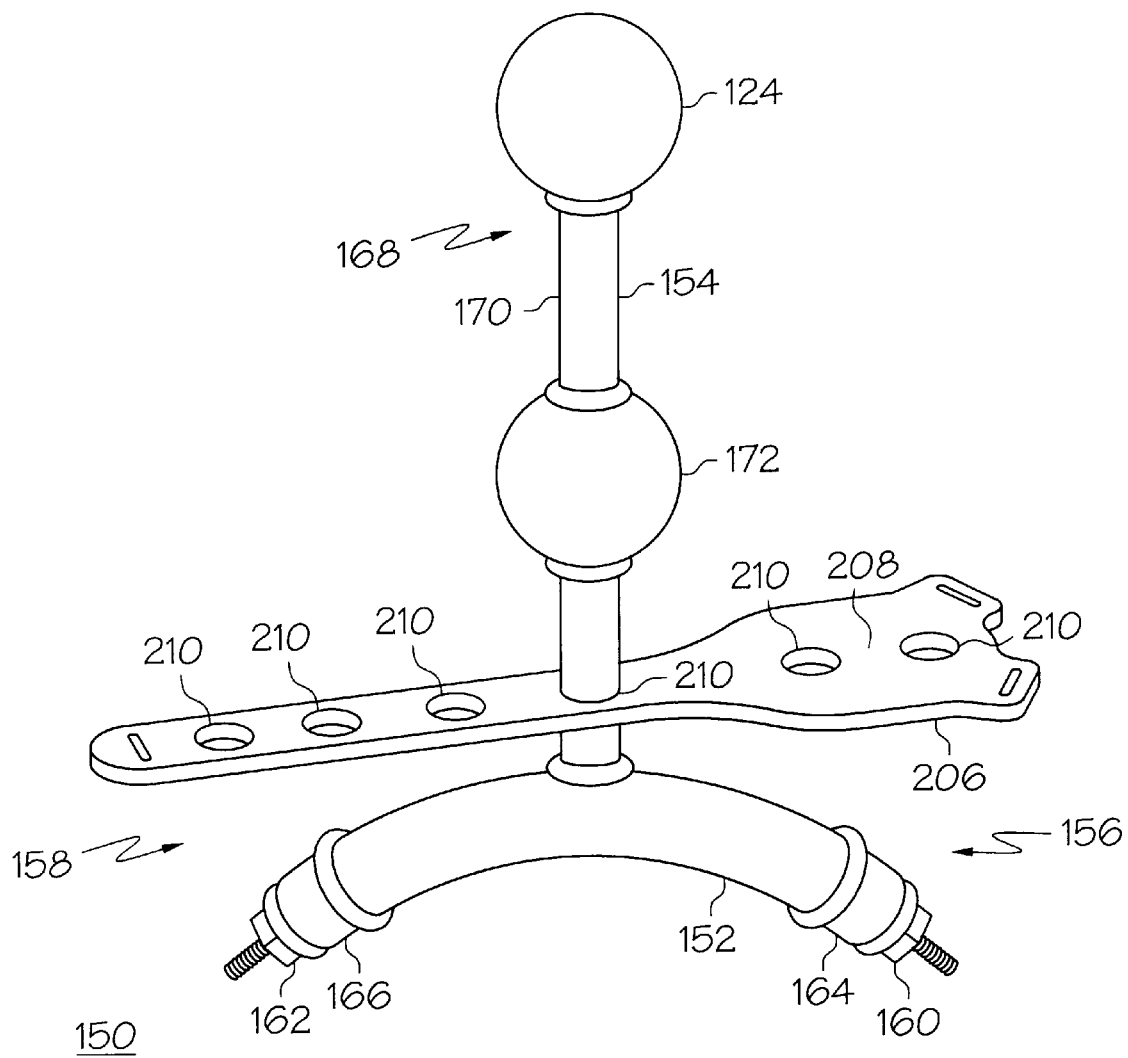
FIG. 12 shows a perspective view of an alternative electrode apparatus in accordance with the present invention.
Figure 13:
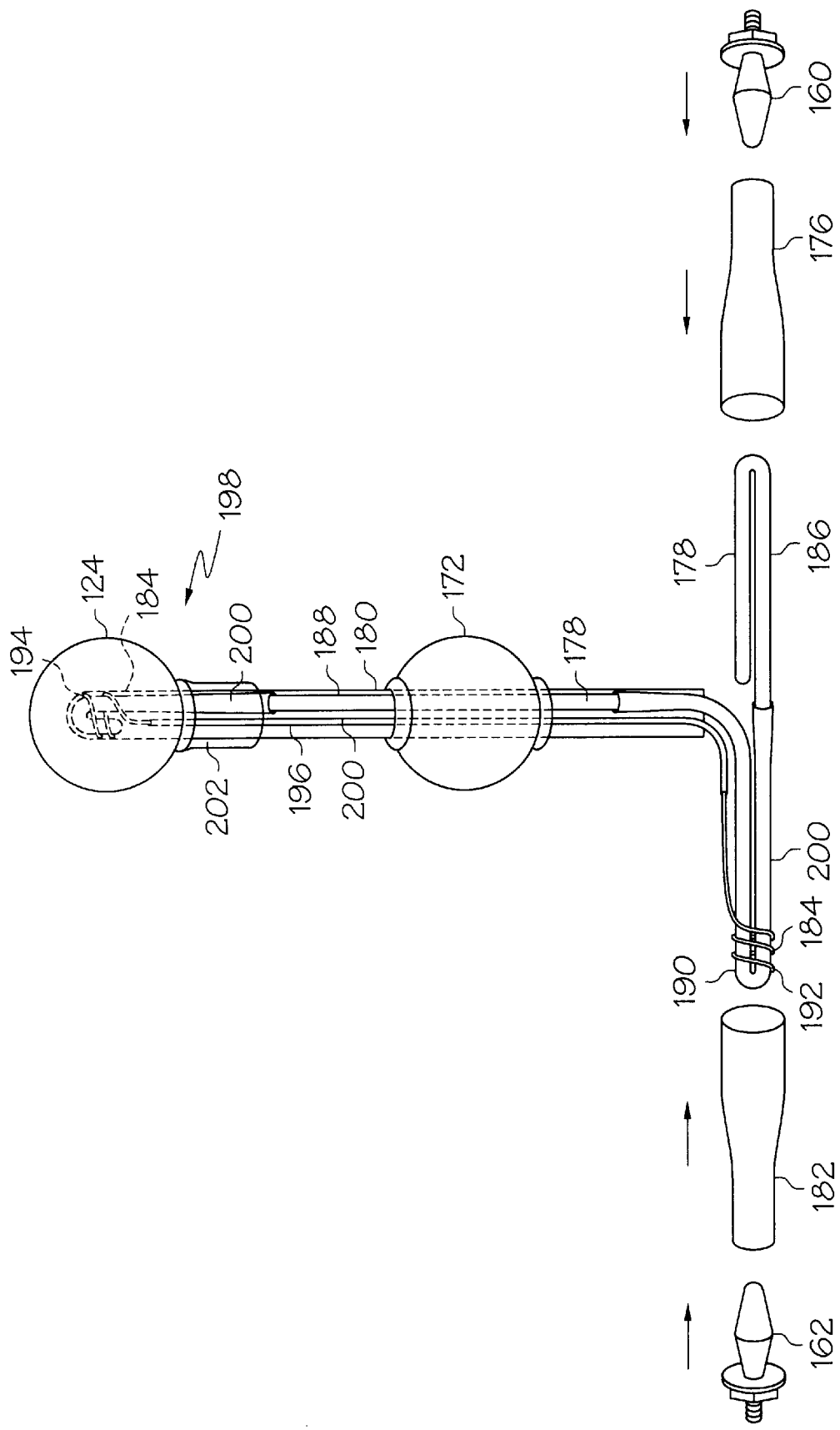
FIG. 13 shows an illustration of a wiring configuration for the electrode apparatus of FIG. 12.

Referring to FIGS. 12–13, FIG. 12 shows a perspective view of an electrode apparatus 150 in accordance with the present invention. FIG. 13 shows an illustration of a wiring configuration for electrode apparatus 150. Electrode apparatus 150 is particularly suited to electrical stimulation of vaginal tissue.

Electrode apparatus 150 includes a flexible, tube-shaped base 152 and an electrode in the form of a stem electrode 154. Base 152 includes first and second ends 156 and 158, respectively, located at opposite ends of the length of base 152. Electrode apparatus 150 further includes a first electrical contact 160, a second electrical contact 162, a first plug 164 connected to first end 156, and a second plug 166 connected to second end 158. First plug 164 includes an opening (not shown) through which a conductive end of first electrical contact 160 extends. Likewise, second plug 166 includes an opening (not shown) through which a conductive end of second electrical contact 162 extends.

A first auxiliary member in the form of conductive spherical endpiece 124 (previously described) is coupled to a distal end 168 of a stem section 170 of electrode 154. A second auxiliary member in the form of a conductive spherical bead 172 having an aperture (not shown) through bead 172 is positioned on stem section 170 of electrode 154. A retainer 174 is also positioned on stem section 170 between base 152 and spherical bead 172. Retainer 174 will be discussed in detail below. Spherical endpiece 124 and spherical bead 172 are positioned to impart concentrated electrical stimuli to particular areas in the vagina.

Spherical bead 172 is in electrical communication with first electrical contact 160. Electrical communication is accomplished through a first conductive sheath 176, a first conductor 178, and carbon-embedded elastomeric material 180 surrounding conductor 178 along stem section 170. Spherical endpiece 124 is in electrical communication with second electrical contact 162. Electrical communication is accomplished through a second conductive sheath 182 and a second conductor 184.

First conductor 178 mechanically supports second conductor 184. However, due to the appropriate utilization of insulative material, spherical endpiece 124 and spherical bead 172 are electrically insulated from one another. First conductor 178 is configured in a manner similar to deformable wire 102 (FIG. 8) of electrode apparatus 96. First conductor 178 includes a first section 186, a second section 188, and a third section 190. Second conductor 184 has a first end 192, a second end 194 and an intermediate section 196.

First end 192 of second conductor 184 is wrapped around third section 190 of first conductor 178. Likewise, second end 194 of second conductor 184 is wrapped around a distal portion 198 of second section 188 of first conductor 178. Third section 178 and distal portion 198 are encased in insulative material 200 so that first and second conductors 178 and 184, respectively, are electrically insulated from one another in those regions.

Intermediate section 196 of second conductor 184 runs substantially parallel to and in contact with second section 188 of first conductor 178. However, intermediate section 196 is encased in insulative material 200 so that first and second conductors 178 and 184, respectively, remain electrically insulated from each other. In addition, an insulator 202 electrically insulates spherical endpiece 124 from conductive elastomeric material 180. Those skilled in the art will readily recognize that first and second conductors 178 and 184, may be fabricated from conventional insulated conductor cable in which the insulation is removed via conventional wirestripping practices to expose the internal conductor.

FIG. 14 shows electrode apparatus 20 in the configuration shown in FIG. 1 used in combination with electrode apparatus 96 in the configuration shown in FIG. 7. Electrode apparatus 20 and electrode apparatus 96 are retained by retainer 174 and a tether system 204 which securely retain electrode apparatus 20 and electrode apparatus 96 in fixed relation to the female genitalia. Referring momentarily to electrode apparatus 150 (FIG. 12), retainer 174 has a first retainer side 206, a second retainer side 208, and orifices 210 running from first retainer side 206 to second retainer side 208. Orifices 210 are sized to allow passage of stem section 170 such that base 152 lies adjacent to first retainer side 206 and stem section 170 extends from second retainer side 208 from one of orifices 210. Although retainer 174 is shown in use with electrode apparatus 150, is should be understood that retainer 174 may also be used in connection with the other electrode apparatuses previously described.

Referring back to FIG. 14, the looped configuration of electrode apparatus 20 shown in FIG. 1 is placed anally and the stem configuration of electrode apparatus 96 shown in FIG. 7 is placed vaginally. Connectors 212 may be attached to their respective electrical contacts 46 of electrode apparatuses 20 and 96. Running directly to and connected to connectors 212 is a conductive line 214. Line 214 has a plug connector 216 which connects electrode apparatuses 20 and 96 to an electrical supply box (not shown).

Figure 15:
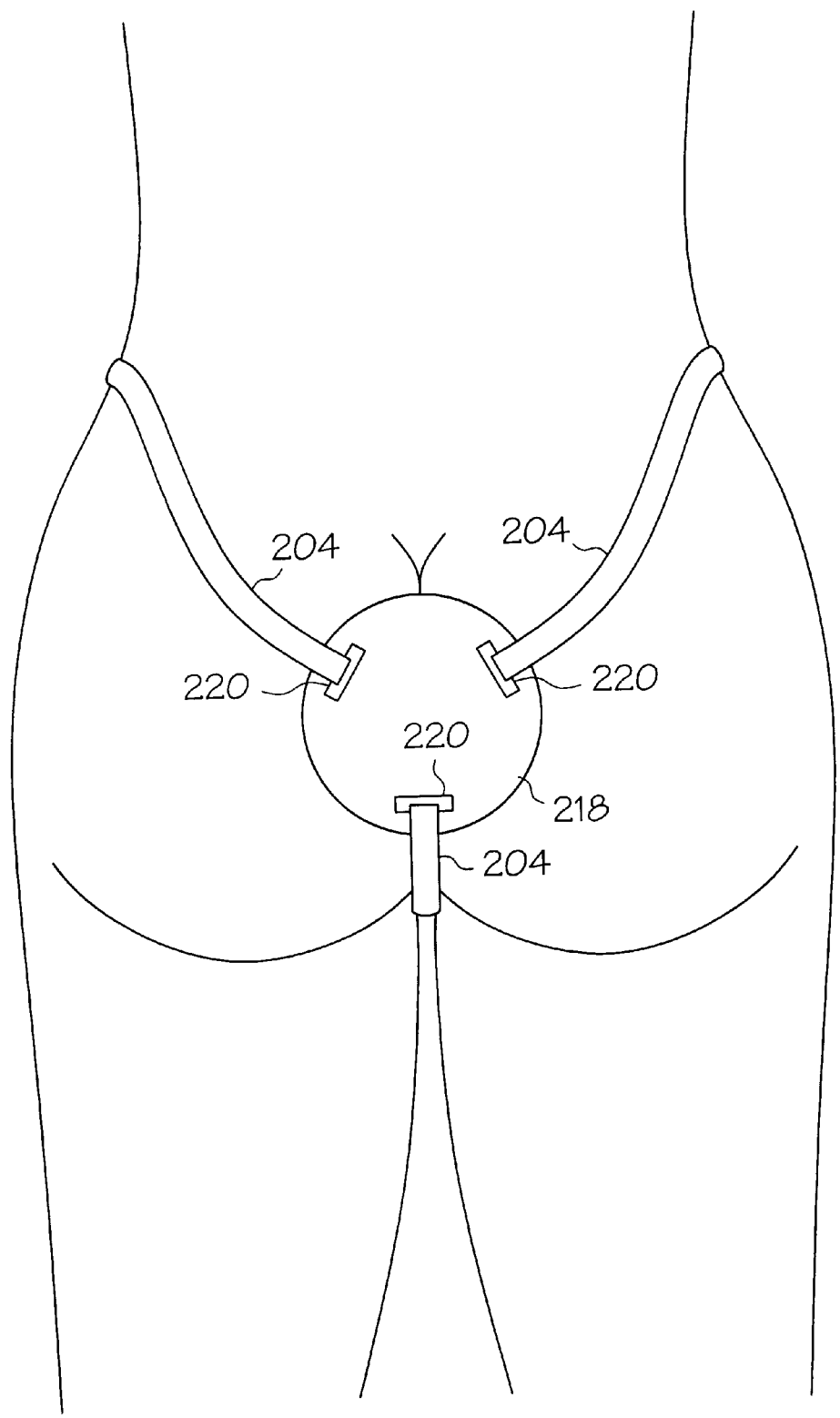
FIG. 15 shows a flexible back plate and tether system in use for retaining electrode apparatuses.

Referring to FIG. 15 in connection with FIG. 14, FIG. 15 shows a flexible back plate 218 and tether system in use for retaining electrode apparatus 20 and electrode apparatus 96. Flexible base plate 218 may be formed from a flexible elastomeric material such as such as silicon, viton, or neoprene. Tether system 204 is formed from three longitudinally stretchable elastic strips, one each of which is routed through one each of three receptacles 220 on flexible base plate 218 and sewn against itself. Likewise, the opposite end of each of the elastic strips of tether system 204 is routed through one each of three receptacles 222 of retainer 174 and sewn against itself. Alternatively, tether system 204 may include adjustable fasteners (not shown) for securing tether system 204 to the body.

When appropriately positioned, retainer 174 retains the electrode devices in their desired position, flexible back plate 218 is positioned proximate the lumbar region of the human body, and tethers 204 are routed from the front of the body to the back of the body around the upper legs and between the buttocks.

Although electrode apparatus 20 and electrode apparatus 96 are shown in use with retainer 174, it should be readily understood that retainer 174 need not be used. The flexible tubular bases described in each of the electrode devices may also be retained by the user's anatomy, such as between the buttocks. In addition, although these devices are shown in use on a female body, it should be understood that they may be used for anal stimulation for a male, and the looped configuration of electrode 20 (FIG. 1) may be used for scrotal or penile stimulation. In particular, the size of the loop may be adjusted by sliding an auxiliary member such as spherical member 72 (FIG. 4) along second section 42 (FIG. 4) of electrode 38 (FIG. 4) so that the loop securely fits about the penis or scrotal tissue.

In summary, the present invention provides an electrical stimulation apparatus that may be adapted for use by both men and women to induce erection and/or orgasm. Electrical stimulation may be applied to the anal, vaginal, and clitoral tissue by means of an electrode that is in a looped configuration or can be configured to be substantially straight or bent and held in an adjustably curved configuration. In addition, auxiliary members such as conductive beads, conductive endpieces, conductive or nonconductive tube shaped coverings, and vibrators may be added to the electrode apparatus to impart specific stimuli in specific regions of the user's anatomy. Furthermore, the electrode apparatuses may be used with a retainer system for securely and comfortably retaining the device proximate a user's genitalia.

Although the preferred embodiments of the invention have been illustrated and described in detail, it will be readily apparent to those skilled in the art that various modifications may be made therein without departing from the spirit of the invention or from the scope of the appended claims. For example, the size and shape of the various auxiliary members may be modified for a particular use.

What is claimed is:

1. An electrode apparatus comprising:
    a base having a length, and first and second ends located at opposite ends of said length, an exterior surface, an interior passage, and a hole running from said exterior surface to said interior passage;
    an electrode having first and second sections, said first section residing in said interior passage, and said second section extending from said exterior surface of said base from said hole;
    an electrical contact in electrical communication with said electrode;
    a first plug connected to said first end, said first plug having an opening through which a portion of said electrical contact extends; and
    a second plug connected to said second end.

2. An electrode apparatus as claimed in claim 1 wherein said base is substantially nonconductive of electrical current.

3. An electrode apparatus as claimed in claim 1 wherein said portion of said electrical contact is an extended segment of said first section of said electrode.

4. An electrode apparatus as claimed in claim 1 wherein:
    said electrical contact further comprises a second portion extending into said interior passage at said second end; and
    said electrode apparatus further comprises an electrically-conductive sheath surrounding said first section and said second portion, said electrically-conductive sheath forming a path for electrical current from said second portion to said first section.

5. An electrode apparatus as claimed in claim 1 wherein a third section of said electrode resides in said interior passage of said base.

6. An electrode apparatus as claimed in claim 5 wherein said first section of said electrode is located proximate said first end of said base, said third section of said electrode is located proximate said second end of said base; and said apparatus further comprises:
    a first sheath retaining said first section; and
    a second sheath retaining said third section, said first and second sheaths being press-fitted into said interior passage of said base.

7. An electrode apparatus as claimed in claim 5 wherein said base is flexible, said first section of said electrode is located proximate said first end of said base, said third section of said electrode is located proximate said second end of said base; and said apparatus further comprises:
    a first O-ring surrounding said base at said first end and configured to apply a force sufficient to retain said first section in said base; and
    a second O-ring surrounding said base at said second end and configured to apply a force sufficient to retain said third section in said base.

8. An electrode apparatus as claimed in claim 5 wherein:
    said base further includes a second hole running from said exterior surface to said interior passage; and
    said third section of said electrode is directed into said interior passage from said second hole, said third section being contiguous with said second section such that said second section extends from said exterior surface of said base from said first hole to said second hole to form a loop.

9. An electrode apparatus as claimed in claim 5 wherein said third section of said electrode is located between and contiguous with said first and second sections, and said third section resides in said interior passage at said second end.

10. An electrode apparatus as claimed in claim 1 further comprising a memory bend wire located within said electrode, said memory bend wire serving to substantially maintain a formed shape of said electrode.

11. An electrode apparatus as claimed in claim 1 wherein said electrode exhibits a length, and said electrode is electrically conductive along its entire length.

12. An electrode apparatus as claimed in claim 1 wherein said electrode is selected from a group consisting of an electrically-conductive tube, an electrically-conductive solid cord, and an insulated conductor cable.

13. An electrode apparatus as claimed in claim 1 further comprising an auxiliary member supported by said second section of said electrode.

14. An electrode apparatus as claimed in claim 13 wherein said auxiliary member is conductive of electrical current for providing an electrical stimulus.

15. An electrode apparatus as claimed in claim 13 wherein said auxiliary member is a vibrator for providing vibratory motion.

16. An electrode apparatus as claimed in claim 13 wherein said auxiliary member is substantially nonconductive of electrical current.

17. An electrode apparatus as claimed in claim 13 further comprising a second auxiliary member, wherein said auxiliary member and said second auxiliary member are tube shaped coverings being slidably adjustable to a plurality of positions along a length of said second section.

18. An electrode apparatus as claimed in claim 13 wherein said second section of said electrode is a stem having a proximal end and a distal end, said proximal end being located proximate said hole, and said auxiliary member being coupled to said distal end.

19. An electrode apparatus as claimed in claim 18 wherein said auxiliary member includes an aperture having a depth which is less than a thickness of said auxiliary member, and said distal end is configured for removable press-fit into said aperture.

20. An electrode apparatus as claimed in claim 18 wherein:
said auxiliary member has a threaded aperture having a depth which is less than a thickness of said auxiliary member; and
said electrode apparatus further comprises a connector having a tubular end and a threaded end, said tubular end being press-fit with said distal end of said second section, and said threaded end being removably mated with said threaded aperture.

21. An electrode apparatus as claimed in claim 13 wherein said auxiliary member has an aperture extending through said auxiliary member and said second section of said electrode is directed through said aperture such that said auxiliary member is slidably adjustable to a plurality of positions along a length of said second section.

22. An electrode apparatus as claimed in claim 21 further comprising a plurality of adjustable stops attachable to said second section, said stops being arranged to prevent movement of said auxiliary member when said member is in one of said plurality of positions.

23. An electrode apparatus as claimed in claim 21 wherein said second section of said electrode exhibits a length, and said electrode is electrically conductive along its entire length, and said electrode apparatus further comprises:
an electrically-nonconductive grommet positioned in said aperture for electrically insulating said second section from said auxiliary member; and
an electrically-conductive snap attachment positioned on an outside surface of said auxiliary member.

24. An electrode apparatus as claimed in claim 21 wherein:
said aperture is a first aperture;
said base has a second hole running from said exterior surface to said interior passage;
said second section of said electrode has a third end and a fourth end, said third end being located proximate said hole, and said fourth end being located proximate said second hole, said second section forming a loop; and
said auxiliary member includes a second aperture extending through said member, said first and second apertures being substantially parallel such that said third end is directed through said first aperture and said fourth end is directed through said second aperture.

25. An electrode apparatus as claimed in claim 13 wherein said auxiliary member is a first auxiliary member, and said electrode apparatus further comprises a second auxiliary member supported by said second section of said electrode, said second auxiliary member being electrically insulated from said first auxiliary member.

26. An electrode apparatus as claimed in claim 25 wherein said second auxiliary member has an second aperture extending through said second auxiliary member and said second section of said electrode is directed through said second aperture such that said auxiliary member is slidably adjustable to a plurality of positions along a length of said second section.

27. An electrode apparatus as claimed in claim 26 further comprising a plurality of adjustable stops attachable to said second section, said stops being arranged to prevent movement of said second auxiliary member when said second member is in one of said plurality of positions.

28. An electrode apparatus as claimed in claim 25 further comprising:
a second electrical contact extending through a second opening in said second plug; and
a second electrode in electrical communication with said second electrical contact, wherein said second auxiliary member is in electrical communication with said second electrode to form a path for the transfer of electrical current from said second electrical contact to said second auxiliary member.

29. An electrode apparatus as claimed in claim 1 further comprising a retainer having a first retainer side and a second retainer side and an orifice running from said first retainer side to said second retainer side wherein said orifice is configured to allow passage of said second section of said electrode such that said base lies adjacent to said first retainer side and said second section extends from said second retainer side of said retainer from said orifice.

30. An electrode apparatus as claimed in claim 29 wherein said electrode apparatus further comprises a tether system for maintaining said retainer in fixed relation to the genitalia of a human body.

31. An electrode apparatus as claimed in claim 30 wherein said
retainer includes three attachment points;
said tether system includes three tethers, one each of said tethers coupling to one each of said attachment points; and
said electrode apparatus further comprises a flexible back plate for adjustable attachment of each of said tethers, said flexible back plate being positioned proximate the lumbar region of the human body.

32. An electrode apparatus comprising:
a base having a length, and first and second ends located at opposite ends of said length, an exterior surface, an interior passage, and first and second holes running from said exterior surface to said interior passage;
an electrode disposed in said base and conductive along a length of said electrode, wherein:
a first section of said electrode resides within said interior passage proximate said first end;
a second section of said electrode extends from said exterior surface of said base from said first hole and extends to said second hole forming a loop; and
a third section of said tube electrode resides within said interior passage proximate said second end;
an electrical contact having a first contact end in electrical communication with said first section;
a first plug connected to said first end, said first plug having an opening through which a second contact end of said electrical contact extends;

a second plug connected to said second end;

a first sheath surrounding said first section and said first contact end, said first sheath being electrically-conductive for forming a path for electrical current from said first contact end to said first section; and a second sheath surrounding said third section, said first and second sheaths being press-fitted into said interior passage of said base.

33. An electrode apparatus as claimed in claim 32 further comprising an auxiliary member having an aperture extending through said auxiliary member, and said second section of said electrode is directed through said aperture such that said auxiliary member is slidably adjustable to a plurality of positions along a length of said second section.

34. An electrode apparatus as claimed in claim 33 wherein said aperture is a first aperture, and said auxiliary member includes a second aperture extending through said member, said first and second apertures being substantially parallel and said second section of said electrode being routed through each of said first and second apertures.

35. An electrode apparatus as claimed in claim 32 wherein said apparatus further comprises:

a first auxiliary member supported by said second section of said electrode; and a second auxiliary member supported by said second section of said electrode, said second auxiliary member being electrically insulated from said first auxiliary member.

36. An electrode apparatus comprising:

a base having a length, and first and second ends located at opposite ends of said length, an exterior surface, an interior passage, and a hole running from said exterior surface to said interior passage;

an electrode disposed in said base wherein:

a first section of said electrode resides in said interior passage; and a second section of said electrode extends from said exterior surface of said base from said hole, said second section being a stem having a proximal end and a distal end, said proximal end being located proximate said hole;

a memory bend wire located within said electrode, said memory bend wire serving to substantially maintain a formed shape of said electrode;

an auxiliary member coupled to said distal end of said second section of said electrode;

an electrical contact in electrical communication with said electrode;

a first plug connected to said first end, said first plug having an opening through which a portion of said electrical contact extends; and a second plug connected to said second end.

37. An electrode apparatus as claimed in claim 36 wherein said auxiliary member is a first auxiliary member, and said electrode apparatus further comprises a second auxiliary member supported by said second section of said electrode, said second auxiliary member being electrically insulated from said first auxiliary member.

38. An electrode apparatus as claimed in claim 36 further comprising a retainer having a first retainer side and a second retainer side and an orifice running from said first retainer side to said second retainer side wherein said orifice is configured to allow passage of said second section of said electrode such that said base lies adjacent to said first retainer side and said second section extends from said second retainer side of said retainer from said orifice.

* * * * *